(12) United States Patent
Oka et al.

(10) Patent No.: US 11,744,556 B2
(45) Date of Patent: Sep. 5, 2023

(54) ULTRASONIC DIAGNOSTIC APPARATUS INCLUDING ULTRASONIC PROBE, CAMERA AND ULTRASONIC IMAGE GENERATOR, CONTROL METHOD OF ULTRASONIC DIAGNOSTIC APPARATUS, AND CONTROL PROGRAM OF ULTRASONIC DIAGNOSTIC APPARATUS FOR PROVIDING CAMERA IMAGE WITH DIFFERENT DISPLAY STYLE DEPENDING ON USAGE

(71) Applicant: Konica Minolta Inc., Tokyo (JP)

(72) Inventors: Toshio Oka, Yokohama (JP); Takashi Sakai, Yokohama (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

(21) Appl. No.: 17/331,729

(22) Filed: May 27, 2021

(65) Prior Publication Data

US 2021/0386405 A1    Dec. 16, 2021

(30) Foreign Application Priority Data

Jun. 16, 2020  (JP) ................................. 2020-103858

(51) Int. Cl.
*A61B 8/08*     (2006.01)
*A61B 8/00*     (2006.01)

(52) U.S. Cl.
CPC ............ *A61B 8/5207* (2013.01); *A61B 8/461* (2013.01); *A61B 8/468* (2013.01); *A61B 8/54* (2013.01)

(58) Field of Classification Search
CPC ....... A61B 8/5207; A61B 8/461; A61B 8/468; A61B 8/469; A61B 8/465
See application file for complete search history.

(56) References Cited

U.S. PATENT DOCUMENTS 10,799,210 B1 * 10/2020 Zhang .................. A61C 9/0086
2009/0203996 A1 * 8/2009 Thiele .................... A61B 8/483
600/447

(Continued)

FOREIGN PATENT DOCUMENTS

JP    2006000400 A  *  1/2006
JP    2007282792 A  * 11/2007

(Continued)

OTHER PUBLICATIONS

JP-2009204817-A (Year: 2009).*
JP-2006000400-A (Year: 2006).*
JP-2007282792-A (Year: 2007).*

*Primary Examiner* — Joel Lamprecht
*Assistant Examiner* — Nyrobi Celestine
(74) *Attorney, Agent, or Firm* — Rankin, Hill & Clark LLP

(57) ABSTRACT

An ultrasonic diagnostic apparatus includes: an ultrasonic probe that transmits/receives ultrasonic waves; a camera that captures a subject; an ultrasonic image generator that generates an ultrasonic image of the subject based on a reception signal acquired from the ultrasonic probe; a first hardware processor that generates a display image including a camera image acquired from the camera and the ultrasonic image acquired from the ultrasonic image generator, and reproducibly saves the display image in a storage; and a second hardware processor that decides a display style of the camera image to be arranged in the display image in accordance with a usage when reading the display image.

16 Claims, 8 Drawing Sheets

(56) References Cited

U.S. PATENT DOCUMENTS

| | | | |
|---|---|---|---|
| 2012/0179039 A1* | 7/2012 | Pelissier | H04N 19/61 |
| | | | 600/443 |
| 2015/0164479 A1* | 6/2015 | Toji | A61B 8/463 |
| | | | 600/440 |
| 2016/0270757 A1* | 9/2016 | Toma | A61B 8/5223 |
| 2017/0112472 A1* | 4/2017 | Song | A61B 8/0875 |
| 2019/0038260 A1* | 2/2019 | Lee | G16H 40/67 |
| 2020/0060658 A1* | 2/2020 | Gafner | A61B 8/5238 |
| 2020/0214672 A1* | 7/2020 | de Jonge | A61B 8/54 |
| 2020/0214680 A1* | 7/2020 | Miyachi | A61B 8/5207 |
| 2020/0214682 A1* | 7/2020 | Zaslavsky | A61B 8/565 |
| 2020/0268344 A1* | 8/2020 | Pelissier | G16H 40/67 |

FOREIGN PATENT DOCUMENTS

| | | |
|---|---|---|
| JP | 2009-207800 A | 9/2009 |
| JP | 2009204817 A * | 9/2009 |

* cited by examiner

ULTRASONIC DIAGNOSTIC APPARATUS INCLUDING ULTRASONIC PROBE, CAMERA AND ULTRASONIC IMAGE GENERATOR, CONTROL METHOD OF ULTRASONIC DIAGNOSTIC APPARATUS, AND CONTROL PROGRAM OF ULTRASONIC DIAGNOSTIC APPARATUS FOR PROVIDING CAMERA IMAGE WITH DIFFERENT DISPLAY STYLE DEPENDING ON USAGE

The entire disclosure of Japanese patent Application No. 2020-103858, filed on Jun. 16, 2020, is incorporated herein by reference in its entirety.

BACKGROUND

Technological Field

The present disclosure relates to an ultrasonic diagnostic apparatus, a control method of the ultrasonic diagnostic apparatus, and a control program of the ultrasonic diagnostic apparatus.

Description of the Related Art

Conventionally, an ultrasonic diagnostic apparatus that generates a tomographic image in a subject by transmitting ultrasonic waves to the inside of the subject and receiving and analyzing the ultrasonic echo is known. The ultrasonic diagnostic apparatus can acquire a two-dimensional or three-dimensional ultrasonic image in real time by scanning ultrasonic waves. Then, by temporally continuously generating ultrasonic images using the ultrasonic diagnostic apparatus, it is possible to observe a moving image of the living body part of the subject.

In recent years, in order to make it possible to recognize the position of an ultrasonic probe and the situation of the operation of a subject from a display image displayed on a monitor, an ultrasonic diagnostic apparatus of this type in which a camera captures both the ultrasonic probe and the subject, and displays, on the monitor, a display image in which the camera image is attached to the ultrasonic image has been conceived.

For example, JP 2009-207800 A discloses a technique in which a camera is connected to an ultrasonic diagnostic apparatus and a camera image under examination is displayed or stored simultaneously with an ultrasonic image. In addition, JP 2009-207800 A discloses a technique in which an examination region is judged or camera zooming on an examination target is performed by utilizing content analysis of the camera image and probe position information at that time.

In the ultrasonic diagnostic apparatus of this type, a camera image displayed together with an ultrasonic image is assumed to have various uses such as (1) usage as a body mark (mark indicating an examination target region of the subject) when the display image is used as a record of the ultrasonic examination, (2) usage for the purpose of reproducing how to apply the ultrasonic probe at the time of reexamination, (3) usage for the examiner to confirm both the position of the ultrasonic probe and the ultrasonic image in a monitor during the ultrasonic examination, and (4) usage for the examiner to explain the coordination between the movement of the body and the movement inside the living body while showing the monitor to the patient.

In this regard, it is preferable that the display style (e.g., normal image display or mirror image display) of the camera image to be displayed together with the ultrasonic image is set differently depending on the usage scene of the ultrasonic diagnostic apparatus.

SUMMARY

Therefore, an object of the present disclosure is to provide an ultrasonic diagnostic apparatus capable of providing image display with higher convenience for a user, a control method of the ultrasonic diagnostic apparatus, and a control program of the ultrasonic diagnostic apparatus.

To achieve the abovementioned object, according to an aspect of the present invention, an ultrasonic diagnostic apparatus reflecting one aspect of the present invention comprises: an ultrasonic probe that transmits/receives ultrasonic waves; a camera that captures a subject; an ultrasonic image generator that generates an ultrasonic image of the subject based on a reception signal acquired from the ultrasonic probe; a first hardware processor that generates a display image including a camera image acquired from the camera and the ultrasonic image acquired from the ultrasonic image generator, and reproducibly saves the display image in a storage; and a second hardware processor that decides a display style of the camera image to be arranged in the display image in accordance with a usage when reading the display image.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Figure 1:
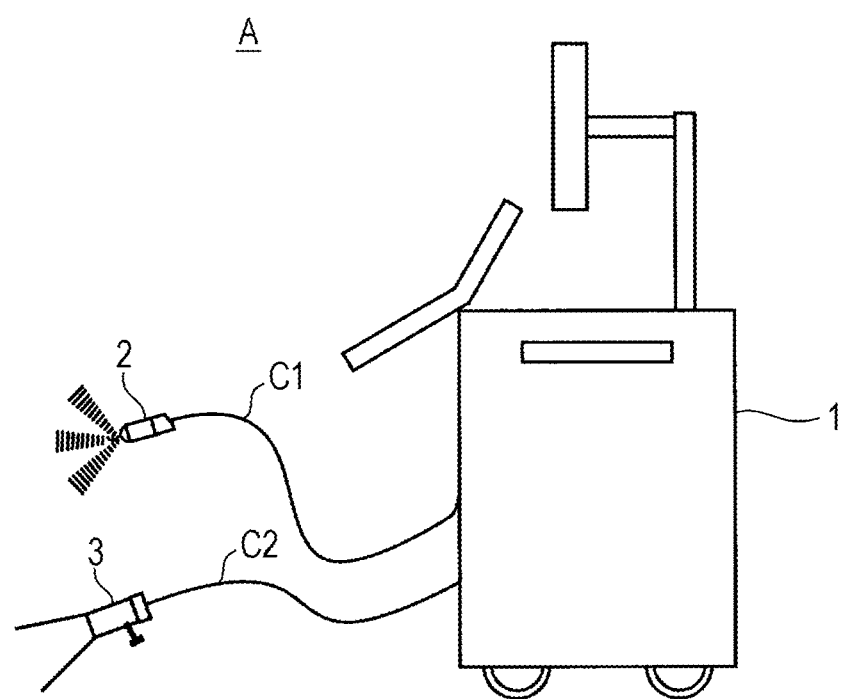
FIG. 1 is a view showing an example of an appearance of an ultrasonic diagnostic apparatus.

Hereinafter, one or more embodiments of the present invention will be described with reference to the drawings. However, the scope of the invention is not limited to the disclosed embodiments. In the present description and the drawings, components having a substantially identical function are given an identical reference numeral, and redundant description thereof is omitted.

[Overall Configuration of Ultrasonic Diagnostic Apparatus]

The configuration of an ultrasonic diagnostic apparatus according to an embodiment of the present invention will be described below with reference to FIGS. 1 to 3.

Figure 2:
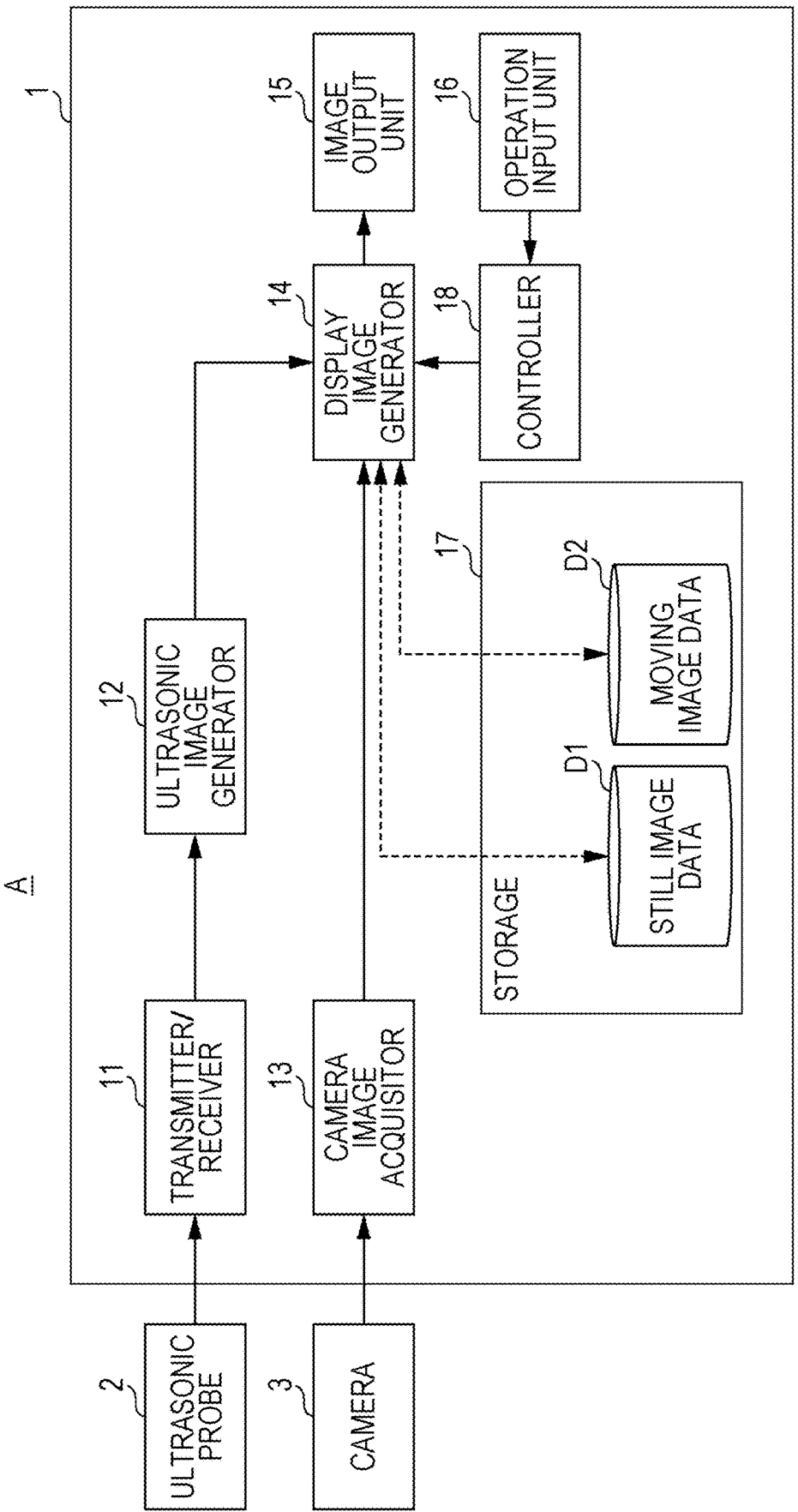
FIG. 2 is a view showing an example of an overall configuration of the ultrasonic diagnostic apparatus.

FIG. 1 is a view showing an example of an appearance of an ultrasonic diagnostic apparatus A. FIG. 2 is a view showing an example of the overall configuration of the ultrasonic diagnostic apparatus A.

Figure 3:
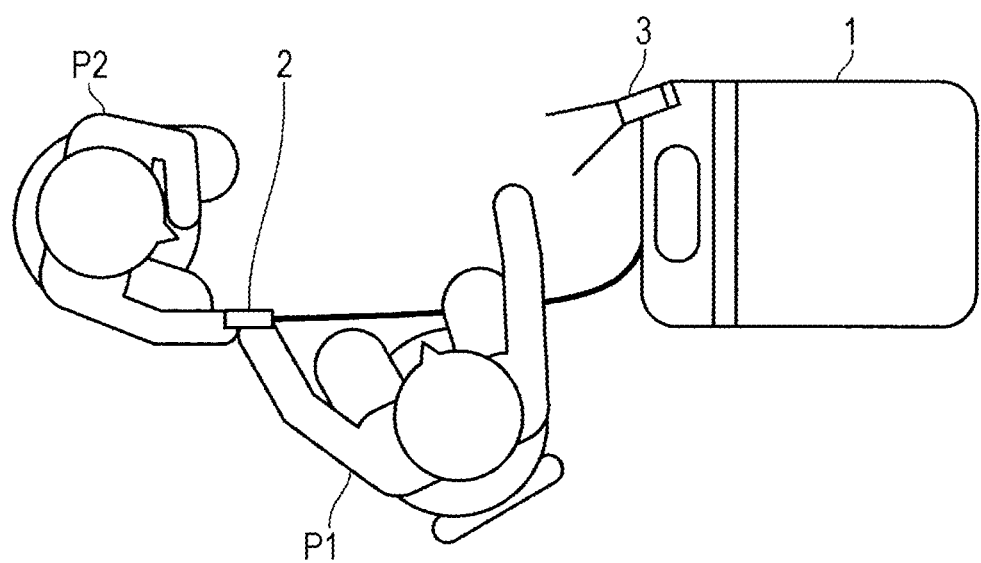
FIG. 3 is a view showing an example of a situation of an ultrasonic examination using the ultrasonic diagnostic apparatus.

FIG. 3 is a view showing an example of the situation of an ultrasonic examination using the ultrasonic diagnostic apparatus A. In FIG. 3, P1 is an examiner (i.e., user), and P2 is a patient (i.e., subject).

The ultrasonic diagnostic apparatus A includes an ultrasonic diagnostic apparatus body 1, an ultrasonic probe 2, and a camera 3. The ultrasonic probe 2 and the camera 3 are connected to the ultrasonic diagnostic apparatus body 1 via cables C1 and C2, respectively.

The ultrasonic probe 2 transmits an ultrasonic beam (here, about 1 to 30 MHz) to the inside of the subject, and functions as an acoustic sensor that receives an ultrasonic echo reflected in the subject among the transmitted ultrasonic beams and converts the ultrasonic echo into an electric signal.

The ultrasonic probe 2 includes, for example, a vibrator train (e.g., piezoelectric vibrator train) in an array, and a channel switcher (e.g., multiplexer) for controlling switching on/off of the drive state of each vibrator of the vibrator train individually or in block units. Each vibrator of the ultrasonic probe 2 converts a voltage pulse generated in the ultrasonic diagnostic apparatus body 1 (transmitter/receiver 11) into an ultrasonic beam, transmits the ultrasonic beam to the subject, receives the ultrasonic echo reflected in the subject, converts the ultrasonic echo into an electric signal (hereinafter referred to as "reception signal"), and outputs the electric signal to the ultrasonic diagnostic apparatus body 1 (transmitter/receiver 11). Then, the vibrators to be driven by the ultrasonic probe 2 are sequentially switched along the scanning direction, thereby executing ultrasonic scanning in the subject.

The camera 3 is a general visible camera such as an optical camera, and generates image data related to a camera image (hereinafter abbreviated as "camera image") by performing AD conversion of an image signal generated by its own imaging device. Then, the camera 3 continuously generates camera images and outputs camera images arranged in time series to the ultrasonic diagnostic apparatus body 1.

The camera 3 is arranged at an appropriate position around the subject so that the subject and the ultrasonic probe 2 can be captured. The arrangement position of the camera 3 is preferably a position where the pressing state (e.g., the position and attitude of the ultrasonic probe 2) of the ultrasonic probe 2 to the subject can be grasped from the camera image.

The ultrasonic diagnostic apparatus body 1 includes the transmitter/receiver 11, an ultrasonic image generator 12, a camera image acquisitor 13, a display image generator 14, an image output unit 15, an operation input unit 16, a storage 17, and a controller 18.

The transmitter/receiver 11 is a drive circuit that causes each vibrator of the ultrasonic probe 2 to transmit/receive ultrasonic waves. The transmitter/receiver 11 transmits a voltage pulse that is a drive signal to each vibrator of the ultrasonic probe 2, and receives and processes an electric signal related to the ultrasonic echo generated by each vibrator of the ultrasonic probe 2.

The ultrasonic image generator 12 performs predetermined signal processing (logarithmic compression, detection, and the like) on the reception signal acquired from the transmitter/receiver 11 to generate image data related to the ultrasonic image (hereinafter abbreviated as "ultrasonic image").

For example, when the ultrasonic probe 2 transmits a pulsed ultrasonic beam toward the depth direction, the ultrasonic image generator 12 sequentially accumulates, in the line memory, the signal intensity of ultrasonic echoes detected subsequently. Then, in response to the scanning of the inside of the subject by the ultrasonic beam from the ultrasonic probe 2, the ultrasonic image generator 12 sequentially accumulates, in each separate line memory, the signal intensity of ultrasonic echoes at each scanning position, and generates two-dimensional data in a frame unit. The ultrasonic image generator 12 generates an ultrasonic image by converting the signal intensity of the ultrasonic echo detected at each position inside the subject into a luminance value.

The ultrasonic image generator 12 temporally continuously generates an ultrasonic image at a frame rate corresponding to the scanning speed of the ultrasonic probe 2.

The camera image acquisitor 13 sequentially acquires camera images from the camera 3. The camera image acquisitor 13 sequentially acquires camera images from the camera 3 at intervals of a frame rate at which the camera 3 generates a camera image, for example.

The display image generator 14 acquires an ultrasonic image from the ultrasonic image generator 12, acquires a camera image from the camera image acquisitor 13, and generates a display image in which the ultrasonic image and the camera image are arranged. Then, the display image generator 14 transmits the data of the generated display image to the image output unit 15.

When the operation mode of the ultrasonic diagnostic apparatus A is a live mode, the display image generator 14 sequentially generates display images in which the real-time ultrasonic image generated by the ultrasonic image generator 12 and the real-time camera image acquired by the camera image acquisitor 13 are arranged, and sequentially updates the display image to be displayed on the image output unit 15.

In this case, the display image generator 14 may specify a temporal correspondence relationship between the timing at which the ultrasonic image is generated and the timing at which the camera image is generated based on the time of the time stamp given to the ultrasonic image and the time of the time stamp given to the camera image, and may generate a display image including the ultrasonic image and the camera image generated at the same or close timing. In this case, the ultrasonic image may be given a time stamp when generated by the ultrasonic image generator 12, and the camera image may be given a time stamp when acquired by the camera image acquisitor 13.

When the operation mode of the ultrasonic diagnostic apparatus A is a still image reproduction mode or a moving image reproduction mode, the display image generator 14 reads still image data D1 or moving image data D2 stored in the storage 17 and generates a display image.

When receiving a still image saving command from the controller 18, the display image generator 14 stores, as the still image data D1 in the storage 17, the data of the display image of one frame held in its frame buffer at the timing of receiving the still image saving command. When receiving a moving image saving command from the controller 18, the display image generator 14 stores, as the moving image data D2 in the storage 17, the data of the display images sequentially generated by itself.

The display image generator 14 is implemented by, for example, a digital arithmetic circuit including a digital signal processor (DSP). However, some or all of the functions of the display image generator 14 may be implemented by the central processing unit (CPU) performing arithmetic processing in accordance with a program, or may be implemented by a dedicated hardware circuit (e.g., ASIC and FPGA).

The image output unit 15 is, for example, a liquid crystal display, a CRT monitor, or the like, and displays a display image generated in the display image generator 14.

The operation input unit 16 is a user interface for a user to perform an input operation, and includes, for example, a push button switch, a keyboard, or a mouse. The operation input unit 16 converts the input operation performed by the user into an operation signal and transmits it to the controller 18.

The user can command, via the operation input unit 16, the ultrasonic diagnostic apparatus A for the operation mode to be executed.

The storage 17 is, for example, an auxiliary storage device such as a hard disk drive (HDD), a solid state drive (SSD), or a flash memory. The storage 17 stores, for example, image format data (not illustrated) for generating a display image, image data of the display image generated in the display image generator 14, and the like. The storage 17 according to the present embodiment stores the moving image data (representing image data of a display image in a moving image format. The same applies hereinafter) D2 and the still image data ((representing image data of a display image in a still image format. The same applies hereinafter) D1.

The controller 18 controls the display image generator 14 so that the display style of the camera image to be arranged in the display image can be switched in accordance with the operation mode of the ultrasonic diagnostic apparatus A (details will be described later). The controller 18 also has a function of acquiring an operation signal from the operation input unit 16 and comprehensively controlling the operation of each unit of the ultrasonic diagnostic apparatus A based on the operation signal.

The controller 18 is a microcomputer that includes, for example, a central processing unit (CPU), a read only memory (ROM), and a random access memory (RAM).

[Display Style Control of Camera Image]

The display image generator 14 is formed to be capable of changing the display style of a camera image to be arranged in a display image. Specifically, the display image generator 14 changes the display style of a camera image to be arranged in a display image based on a control command related to the operation mode of the ultrasonic diagnostic apparatus A to be received from the controller 18.

At this time, the display image generator 14 preferably adds, to the display image, an explanatory image (see image R3 in FIGS. 4 and 5) indicating the mode of the display style of the camera image currently arranged in the display image. This allows the user to recognize in an error-free manner the display style of the currently displayed camera image.

Figure 4:
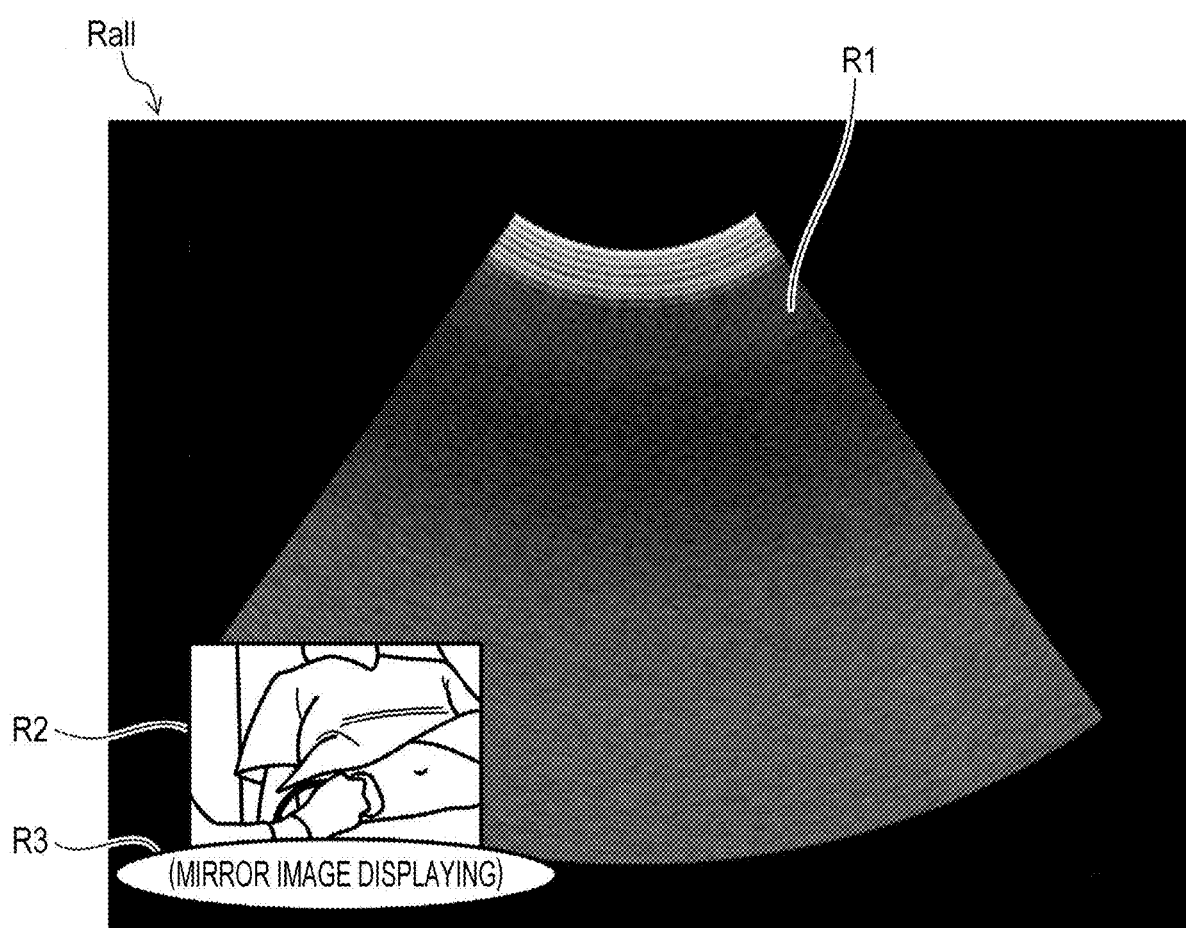
FIG. 4 is a view showing an example of a display image generated by a display image generator (camera image: mirror image display)
Figure 5:
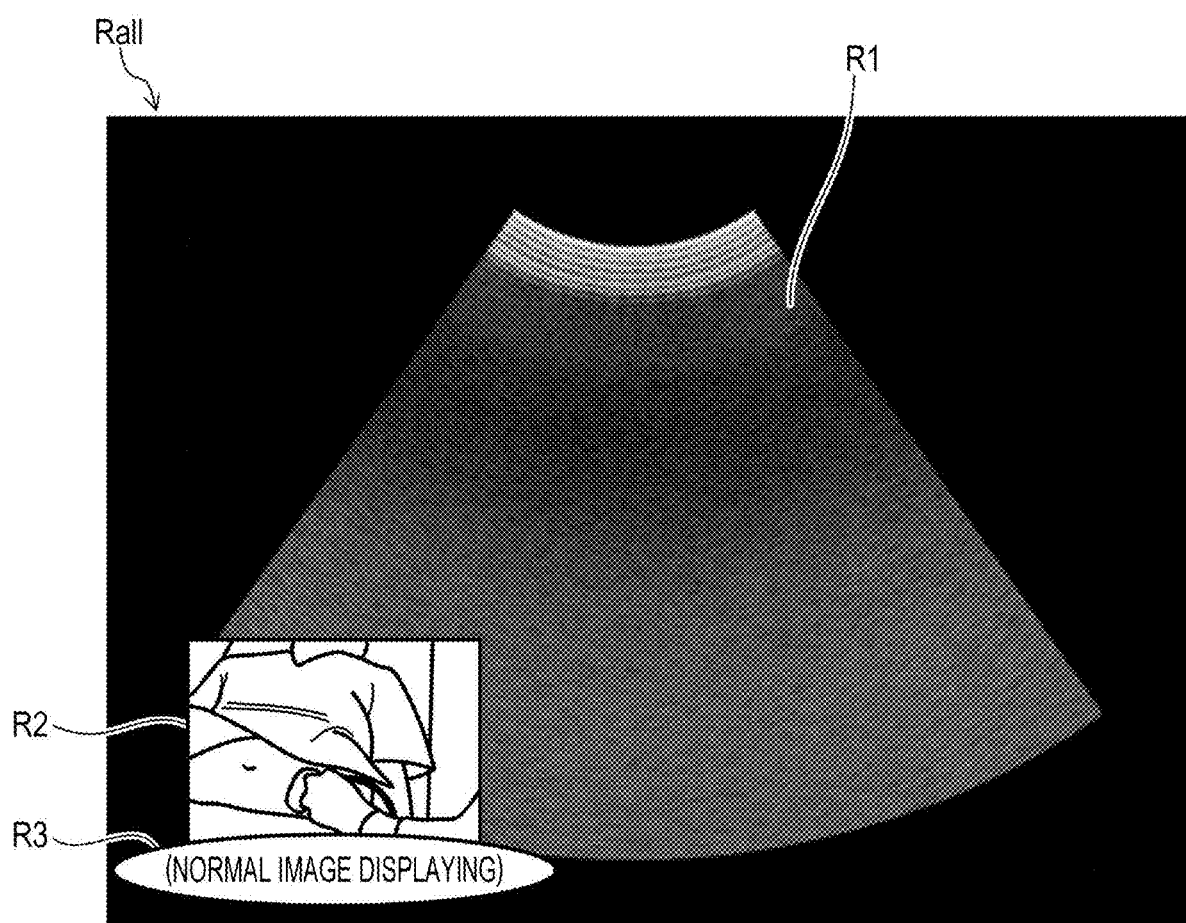
FIG. 5 is a view showing an example of a display image generated by the display image generator (camera image: normal image display)

FIGS. 4 and 5 are views showing an example of a display image generated by the display image generator 14. The display image of FIG. 4 and the display image of FIG. 5 are display images generated at the same timing. FIG. 4 indicates a state in which the camera image is displayed as a mirror image, and FIG. 5 indicates a state in which the camera image is displayed as a normal image. In FIGS. 4 and 5, Rall represents the entire display image, R1 represents an ultrasonic image, R2 represents a camera image, and R3 represents an explanatory image.

Here, the display style of the camera image to be switched by the display image generator 14 is typically, as shown in FIGS. 4 and 5, the display style related to mirror image display (i.e., horizontally inverted display) or normal image display (i.e., horizontally non-inverted display). Based on a control command from the controller 18, the display image generator 14 switches whether the camera image obtained by capturing is displayed as a normal image or the camera image obtained by capturing is displayed as a mirror image. Such control is performed because, depending on the usage scene of the ultrasonic diagnostic apparatus A, the convenience for the user varies between the camera image displayed as a mirror image and the camera image displayed as a normal image.

The operation mode of the ultrasonic diagnostic apparatus A serving as a reference for deciding the display style of the camera image includes, for example, a live mode, a freeze mode, a moving image reproduction mode, and a still image reproduction mode.

The live mode is an operation mode in which the ultrasonic probe 2 executes transmission/reception of ultrasonic waves and captures a tomographic image of the subject. In the live mode, the ultrasonic diagnostic apparatus A updates in real time the ultrasonic image of the subject and the display image including the camera image.

The freeze mode is a mode in which transmission/reception of ultrasonic waves in the ultrasonic probe 2 is stopped by, as a trigger, a freeze command having been input by the user during the live mode. In the freeze mode, the display image generated last in the live mode is held in a frame buffer of the display image generator 14, and the display image generator 14 stops updating the display image.

The still image reproduction mode is a mode in which the display image generator 14 reads the still image data D1 of the display image generated during the past ultrasonic examination from the storage 17 and displays the still image data D1 in the image output unit 15. Recording of a still image of an ultrasonic image is executed, for example, based on a still image saving command having been input by the user during the freeze mode, and the image data of one display image generated in the display image generator 14 at this time is stored in the storage 17 as the still image data D1.

The moving image reproduction mode is a mode in which the display image generator 14 reads the moving image data D2 of the display image generated during the past ultrasonic examination from the storage 17, and the image output unit 15 reproduces the moving image. Recording of a moving image of an ultrasonic image is executed, for example, based on a moving image saving command having been input by the user during the live mode, and the image data of time-series display images generated in the display image generator 14 at this time is stored in the storage 17 as the moving image data D2.

Specifically, the display image generator 14 changes the display style of the camera image to be arranged in the display image as follows.

When the operation mode of the ultrasonic diagnostic apparatus A is the live mode, the display image generator 14 displays, as a mirror image, a camera image to be arranged in the display image. When the operation mode of the ultrasonic diagnostic apparatus A is the freeze mode, the display image generator 14 displays, as a normal image, a camera image to be arranged in the display image. When the operation mode of the ultrasonic diagnostic apparatus A is the still image reproduction mode, the display image generator 14 displays, as a normal image, a camera image to be arranged in the display image. When the operation mode of the ultrasonic diagnostic apparatus A is the moving image reproduction mode, the display image generator 14 displays, as a mirror image, a camera image to be arranged in the display image.

When the operation mode of the ultrasonic diagnostic apparatus A is the live mode, in general, the user is in a situation of moving the ultrasonic probe 2 while visually recognizing the display image displayed on the image output unit 15. At this time, since the ultrasonic diagnostic apparatus body 1 is generally arranged on the opposite side or the lateral side of the subject as viewed from the user (see FIG. 3), if the camera image is not displayed as a mirror image, the moving direction of the ultrasonic probe 2 may appear to be opposite to the direction intended by the user when the camera image is viewed. In other words, by displaying the camera image as a mirror image at this time, the user obtains a feeling of moving the ultrasonic probe 2 while visually recognizing the mirror, and hence the user can intuitively move the ultrasonic probe 2 while visually recognizing the display image (i.e., camera image) displayed on the image output unit 15.

The moving image reproduction mode of the ultrasonic diagnostic apparatus A is generally used for the usage of reproducing an ultrasonic examination carried out in the past. In the moving image reproduction mode, similarly to the case where the ultrasonic diagnostic apparatus A is operated in the live mode, the user is supposed to move the ultrasonic probe 2 while visually recognizing the display image (camera image) displayed on the image output unit 15 in a state where the ultrasonic diagnostic apparatus body 1 is arranged on the opposite side or the lateral side of the subject as viewed from the user. Therefore, even when the ultrasonic diagnostic apparatus A is operated in the moving image reproduction mode, as in the case where the ultrasonic diagnostic apparatus A is operated in the live mode, it is preferable that a camera image as an inverted mirror image is displayed on the image output unit 15.

On the other hand, when the operation mode of the ultrasonic diagnostic apparatus A is the freeze mode or the still image reproduction mode, in general, the user does not perform the movement operation of the ultrasonic probe 2, and is in a situation of objectively observing the pressing position of the ultrasonic probe 2 against the subject, the attitude of the ultrasonic probe 2, and the like by visually recognizing the display image displayed on the image output unit 15. At this time, if the camera image is displayed as a mirror image, the user visually recognizing the camera image displayed in the display image has a risk of recognizing, in a horizontally inverted manner, the position at which the ultrasonic probe 2 is pressed against the subject. From this point of view, when the operation mode of the ultrasonic diagnostic apparatus A is the freeze mode or the still image reproduction mode, the camera image displayed in the display image is preferably displayed as a normal image.

From this point of view, in accordance with the operation mode of the ultrasonic diagnostic apparatus A, the display image generator 14 switches the display style for arranging the camera image on the display image between the mirror image display and the normal image display.

The generation processing of the display image by the display image generator 14 is the same as the known method. The display image generator 14 generates a display image by embedding, in image format data of the display image, for example, an ultrasonic image acquired from the ultrasonic image generator 12 and embedding a camera image acquired from the camera image acquisitor 13. When embedding the camera image in the display image, the display image generator 14 switches the camera image between mirror image display and normal image display in accordance with the operation mode of the ultrasonic diagnostic apparatus A.

When there is a saving command of a still image, the display image generator 14 stores, in the storage 17 as the still image data D1, the display image in which the camera image and the ultrasonic image having been set to normal image display are embedded in the image format data of the display image. On the other hand, when there is a saving command of a moving image, the display image generator 14 stores, in the storage 17 as the moving image data D2, the display image in which the camera image and the ultrasonic image having been set to mirror image display are embedded in the image format data of the display image. Thus, in the still image reproduction mode, the display image generator 14 outputs a display image in which the camera image is displayed as a normal image, and in the moving image reproduction mode, the display image generator 14 outputs a display image in which the camera image is displayed as a mirror image.

The processing of arranging the camera image in the display image by the display image generator 14 may be to embed the camera image in a predetermined position of the image format data of the display image, or may be to display, in a superimposing manner or side by side, the camera image in an appropriate position regardless of the image format data of the display image. The same applies to the processing of arranging the ultrasonic image in the display image by the display image generator 14.

(Operation of Ultrasonic Diagnostic Apparatus)

Figure 6:
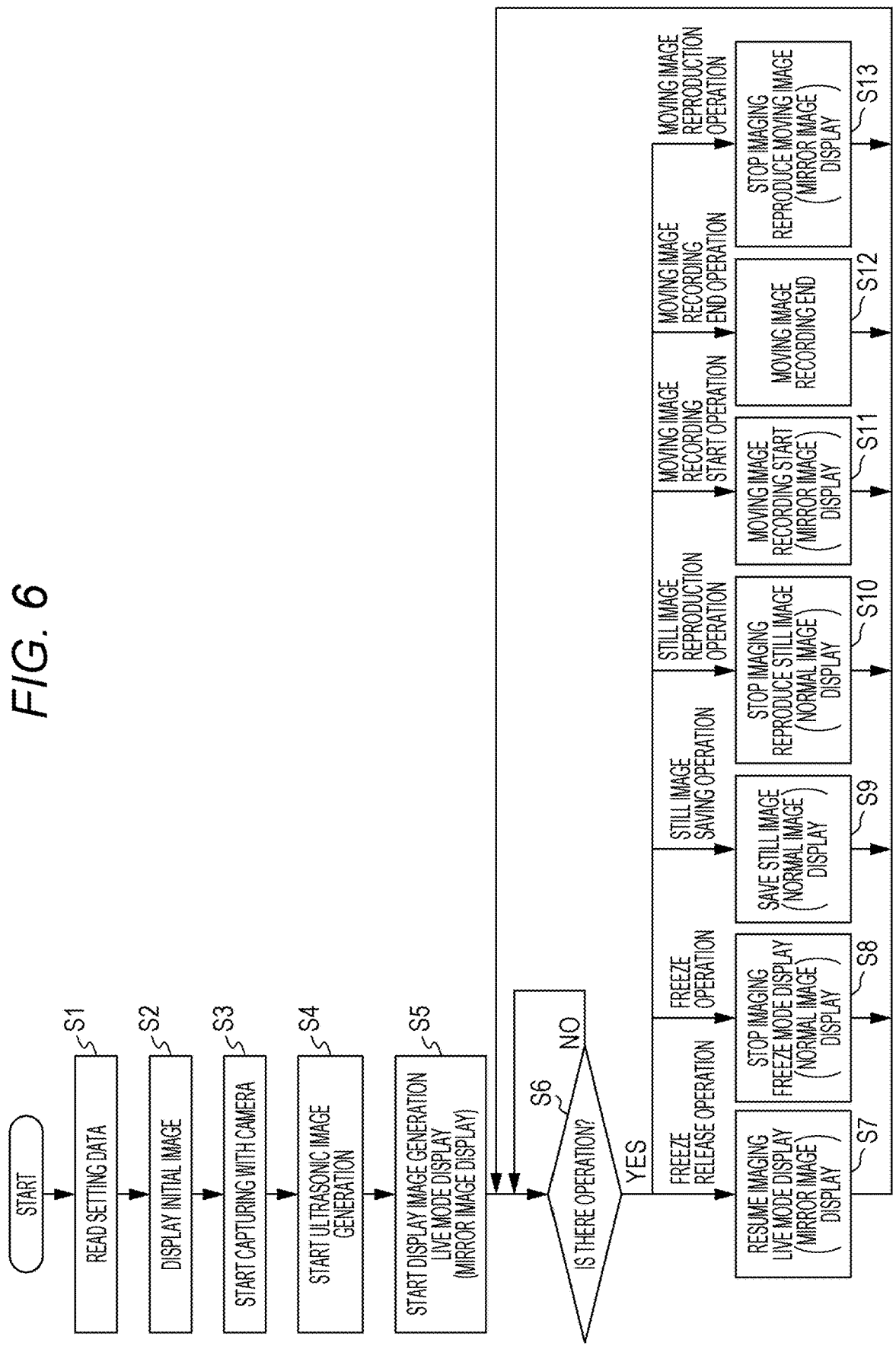
FIG. 6 is a view showing an example of an operation flow of the ultrasonic diagnostic apparatus.

FIG. 6 is a view showing an example of the operation flow of the ultrasonic diagnostic apparatus A. Each step shown in FIG. 6 is executed in accordance with a computer program, for example, by the controller 18 of the ultrasonic diagnostic apparatus A.

When executing an ultrasonic diagnostic program, the controller 18 first reads setting data (not illustrated) such as measurement conditions and display settings, and sets the setting data as variables in various processing (step S1).

Next, the controller 18 causes the display image generator 14 to generate an initial screen of the display image, and the image output unit 15 to display it (step S2).

Next, the controller 18 causes the camera 3 to start capturing, and causes the camera image acquisitor 13 to sequentially acquire camera images generated by the camera 3 (step S3).

Next, the controller 18 causes the ultrasonic probe 2 to start transmitting/receiving ultrasonic waves, and causes the ultrasonic image generator 12 to start generating an ultrasonic image (step S4).

Next, the controller 18 causes the display image generator 14 to embed the ultrasonic image acquired from the ultrasonic image generator 12 in the image format data of the display image, and to start the generation processing of the display image in which the camera image acquired from the camera image acquisitor 13 is embedded (step S5). The controller 18 outputs a display command signal to the image output unit 15, and causes the image output unit 15 to display the display image generated by the display image generator 14. At this time, the display image generated in the display image generator 14 is a display image in the live mode in which the camera image is displayed as a mirror image.

Next, the controller 18 determines whether or not there has been an input operation to the operation input unit 16 (step S6), and waits for an input operation to the operation input unit 16 (step S6: NO). If an input operation to the operation input unit 16 has been made (step S6: YES), the controller 18 performs conditional branching based on the content of the operation signal, and executes processing corresponding to each of a freeze operation, a freeze release operation, a still image saving operation, a still image reproduction operation, a moving image saving start operation, a moving image saving end operation, and a moving image reproduction operation (steps S7 to S13).

In step S6, the controller 18 determines whether any of the operation buttons of the operation input unit 16 provided separately has been pressed, in order to perform each of the freeze operation, the freeze release operation, the still image saving operation, the still image reproduction operation, the moving image saving start operation, the moving image saving end operation, and the moving image reproduction operation. If any of the operation buttons is pressed, the operation is stored in a register as an identifiable operation signal, for example, and input to the controller 18 via the register.

Here, the processing corresponding to each of the freeze operation, the freeze release operation, the still image saving operation, the still image reproduction operation, the moving image saving start operation, the moving image saving end operation, and the moving image reproduction operation in a case where an input operation to the operation input unit 16 is made will be explained (steps S7 to S13).

If the freeze release operation is performed, the controller 18 resumes the imaging operation by the ultrasonic probe 2 set to the freeze mode by the freeze operation. At this time, the controller 18 causes the display image generator 14 to generate a display image in the live mode in which the camera image is displayed as a mirror image (step S7).

If the freeze operation is performed, the controller 18 causes the transmitter/receiver 11 to stop the imaging operation by the ultrasonic probe 2. At this time, the controller 18 causes the display image generator 14 to generate a display image in the freeze mode in which the camera image is displayed as a normal image (step S8). At this time, the frame buffer of the display image generator 14 holds the ultrasonic image generated last during the live mode, and the image output unit 15 displays a still image of the ultrasonic image.

If the still image saving operation is performed, the controller 18 outputs a saving instruction signal to the display image generator 14, and causes the display image generator 14 to generate an ultrasonic image for one frame as a target to be saved. By encoding, into JPEG format, image data of one frame when the still image saving operation is performed, for example, the display image generator 14 generates the still image data D1 of the target to be saved, and stores it in the storage 17. At this time, the display image generator 14 saves, in the storage 17 as the still image data D1, the display image in which the camera image is displayed as a normal image (step S9).

If the still image reproduction operation is performed, the controller 18 causes the transmitter/receiver 11 to stop the imaging operation by the ultrasonic probe 2. At this time, the controller 18 causes the display image generator 14 to read the still image data D1 selected by the user from the storage 17, and causes the image output unit 15 to display the display image stored as the still image data D1. Since the still image data D1 is stored as a display image in which the camera image is displayed as a normal image, in this still image reproduction mode, the display image that the display image generator 14 outputs to the image output unit 15 is also brought into a state where the camera image is displayed as a normal image (step S10).

If the moving image saving start operation is performed, the controller 18 causes the display image generator 14 to start generation of moving image data as a target to be saved. By encoding, into MPEG format, image data of a plurality of consecutive frames, for example, the display image generator 14 generates the moving image data D2 of the target to be saved, and stores it in the storage 17. At this time, the display image generator 14 saves, in the storage 17 as the moving image data D2, the display image in which the camera image is displayed as a mirror image (step S11).

If the moving image saving end operation is performed, the controller 18 causes the display image generator 14 to stop recording of the moving image data started by the moving image saving start operation (step S12).

If the moving image reproduction operation is performed, the controller 18 causes the transmitter/receiver 11 to stop the imaging operation by the ultrasonic probe 2. At this time, the controller 18 causes the display image generator 14 to read the moving image data D2 selected by the user from the storage 17, and causes the image output unit 15 to sequentially display the display images stored as the moving image data D2. Since the moving image data D2 is stored as a display image in which the camera image is displayed as a mirror image, in this moving image reproduction mode, the display image that the display image generator 14 outputs to the image output unit 15 is also brought into a state where the camera image is displayed as a mirror image (step S13).

If an input operation to the operation input unit 16 is performed (step S6: YES), the controller 18 executes the processing steps S7 to S13 corresponding to these input operations, and then returns to step S6 again to continue the same processing as described above.

[Effects]

As described above, according to the ultrasonic diagnostic apparatus A according to the present embodiment, it is possible to store an image in the storage 17 by switching the display style (e.g., normal image display or mirror image display) of the camera image to be arranged in the display image in accordance with the usage at the time of reading of the display image of the target to be saved.

Thus, it is possible to provide image display with higher convenience for the user in the moving image reproduction mode or the still image reproduction mode.

(Variation 1)

In the mode shown in the above embodiment, the camera image is arranged in the display image as normal image display and stored in the storage 17 as the still image data D1 when the user performs the still image saving operation. In this regard, the ultrasonic diagnostic apparatus according to Variation 1 is different from that according to the above embodiment in that the still image data D1 related to the display image is saved by, as a trigger, an input operation of annotation by the user or an input operation for setting the probe mark by the user.

Figure 7:
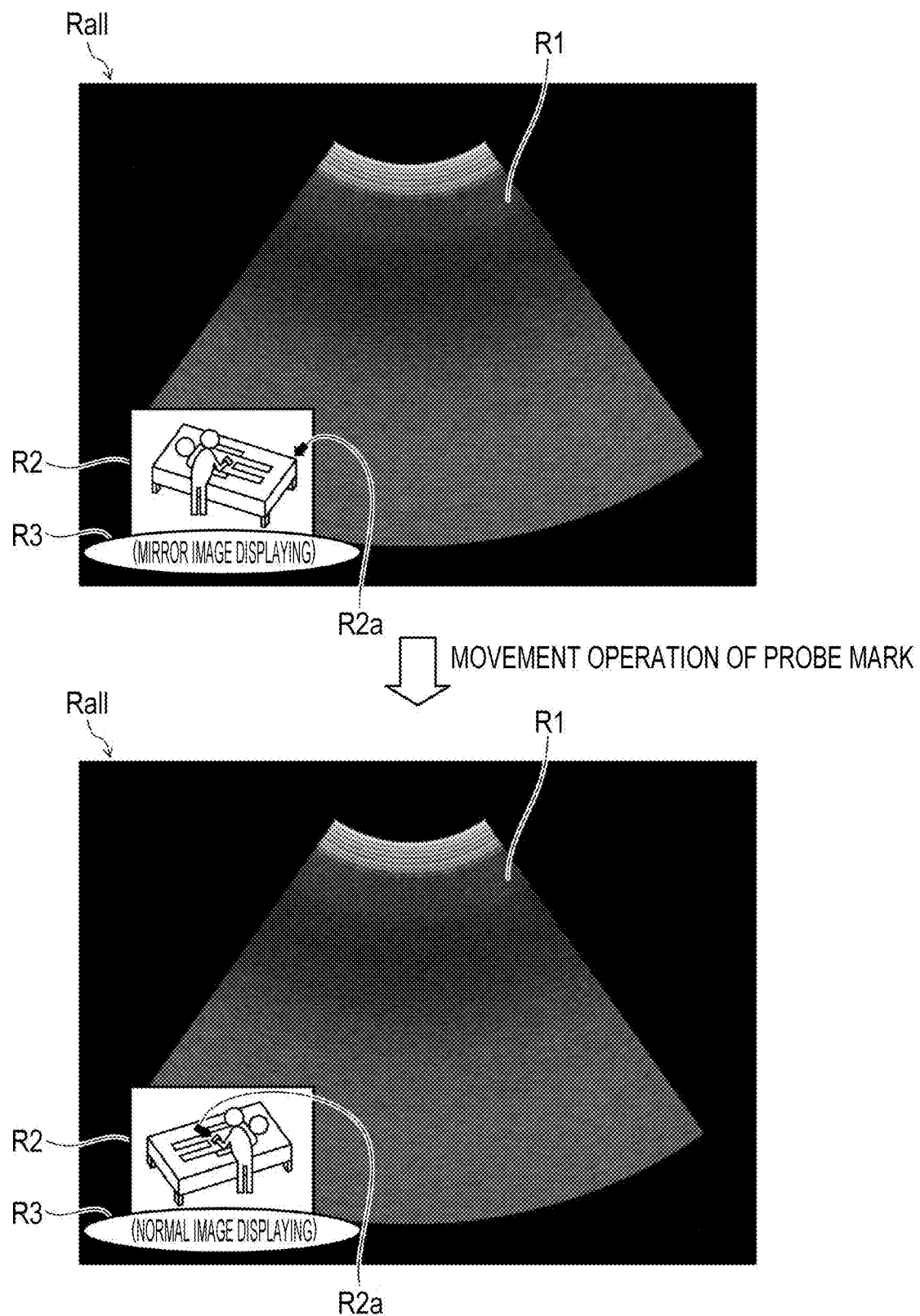
FIG. 7 is a view explaining a probe mark setting function.
Figure 8:
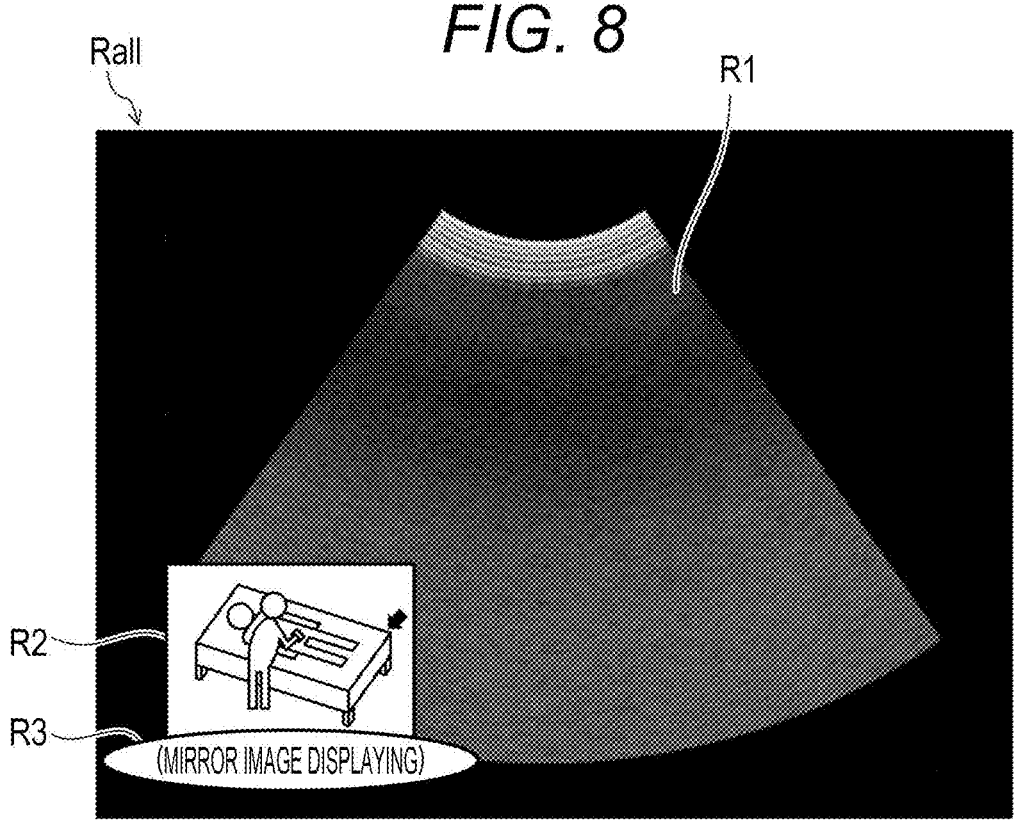
FIG. 8 is a view explaining an annotation setting function.
Figure 8:
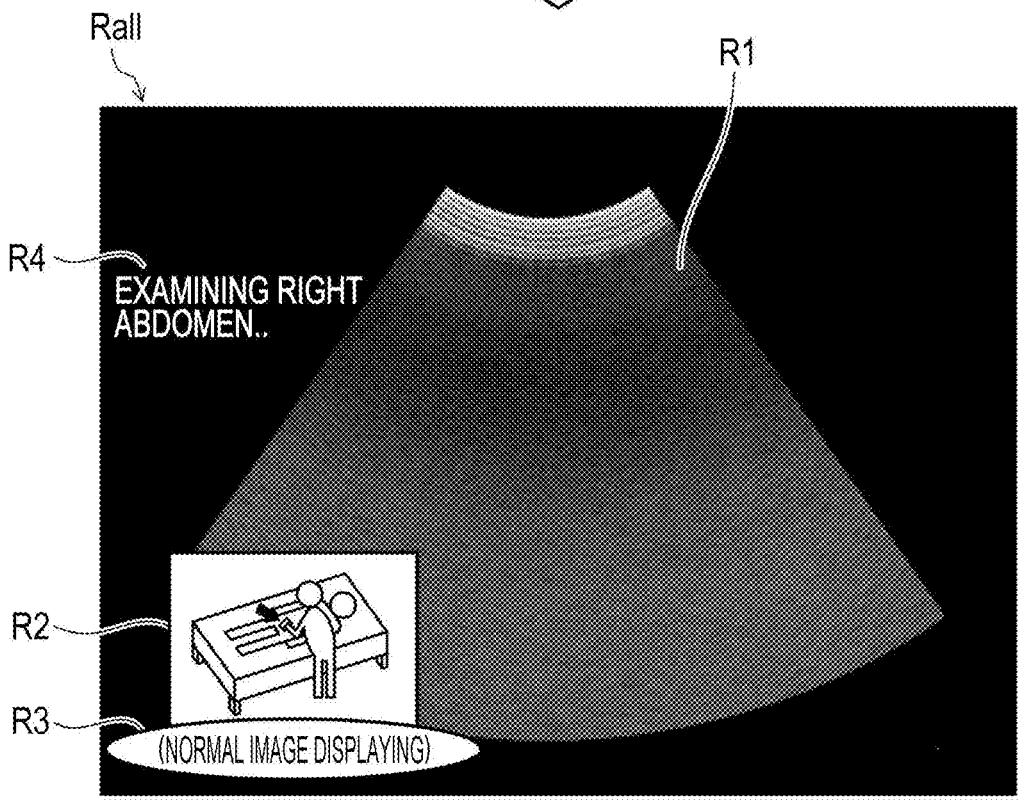

FIG. 7 is a view explaining the probe mark setting function. FIG. 8 is a view explaining the annotation setting function.

The camera image arranged in the display image can function as a body mark indicating the examination target region. However, depending on the capturing position of the camera 3, the position of the ultrasonic probe 2 is sometimes difficult to visually recognize in the camera image. For example, in FIGS. 7 and 8, the distance between the camera 3 and the subject is long, and the position of the ultrasonic probe 2 in the camera image is difficult to visually recognize.

The display image generator 14 according to Variation 1 has a configuration in which a probe mark (see R2a in FIG. 7) can be given to a desired position on the camera image of the display image by the user's input operation so that the position of the ultrasonic probe 2 in the camera image can be identified even in such a case. The display image generator 14 according to Variation 1 has a configuration in which text annotation (see R4 in FIG. 8) can be given in the display image by the user's input operation. The configuration is useful in particular when the display image is used as a record of an ultrasonic examination.

However, in a case where the user performs the input operation of annotation or in a case where the user performs the input operation for setting the body mark, the user is brought into a situation of gazing the display image displayed on the image output unit 15 rather than a situation of moving the ultrasonic probe 2 while visually recognizing the display image displayed on the image output unit 15. From this point of view, in such a case, the display image generator 14 according to Variation 1 switches the camera image from the mirror image display to the normal image display even if the operation mode of the ultrasonic diagnostic apparatus A is the live mode.

Then, in such a case, in general, the user is in a situation of desiring to save the display image. Therefore, when the user performs an input operation of annotation or the user performs an input operation for setting a probe mark, the display image generator 14 according to Variation 1 saves the display image as the still image data D1 on an assumption that a still image saving operation has been performed.

As described above, according to the ultrasonic diagnostic apparatus A according to Variation 1, since the display style of the camera image to be arranged in the display image is controlled by referring to the input operation information of the user in addition to the operation mode of the ultrasonic diagnostic apparatus A, it is possible to save a display image with higher convenience for the user.

(Variation 2)

In the above embodiment, the still image saving operation for saving the display image as a still image and the moving image saving operation for saving the display image as a moving image are separate. However, whether to save the display image as a still image or whether to save the display image as a moving image may be switched by either the live mode or the freeze mode of the operation mode of the ultrasonic diagnostic apparatus A when there has been an image saving operation from the user.

As a general usage mode of the ultrasonic diagnostic apparatus A, the moving image saving operation is performed when the operation mode of the ultrasonic diagnostic apparatus A is the live mode, and the still image saving operation is performed when the operation mode of the ultrasonic diagnostic apparatus A is the freeze mode.

From this point of view, the display image generator 14 according to Variation 2 saves, as the moving image data D2, the temporally continuously generated display image if there has been an image saving operation from the user when the operation mode of the ultrasonic diagnostic apparatus A is the live mode. If there has been an image saving operation from the user when the operation mode of the ultrasonic diagnostic apparatus A is the freeze mode, the display image generator 14 according to Variation 2 saves, as the still image data D1, one display image stored in the frame buffer of the display image generator 14.

As described above, the ultrasonic diagnostic apparatus A according to Variation 2 is useful in that the number of operation buttons can be reduced.

(Variation 3)

In the mode shown in the above embodiment, the display image is saved in a state where the camera image is set to normal image display when the display image is saved as a still image, and the display image is saved in a state where the camera image is set to mirror image display when the display image is saved as a moving image.

However, some users find it troublesome that the display style of the camera image is different between the moving image reproduction mode and the still image reproduction mode, and the needs for the display style of the camera image may vary depending on each user. From this point of view, the display style of the camera image to be arranged in the display image of the target to be saved may be settable by the user in advance in association with the usage when reading the display image.

Other Embodiments

The present invention is not limited to the above-described embodiment, and various variation modes can be conceived.

For example, in the above embodiment, the display style related to normal image display and mirror image display is presented as an example of the display style of the camera image to be changed by the display image generator 14. However, the display style of the camera image to be changed by the display image generator 14 may be a display style related to black and white display and color display, or a display style related to large-screen display and reduced-screen display.

According to the ultrasonic diagnostic apparatus according to the present disclosure, it is possible to provide image display with higher convenience for the user.

Although embodiments of the present invention have been described and illustrated in detail, the disclosed embodiments are made for purposes of illustration and example only and not limitation. The scope of the present invention should be interpreted by terms of the appended claims. The techniques described in the claims include various variations and modifications of the embodiments illustrated above.

What is claimed is:

1. An ultrasonic diagnostic apparatus comprising:
   an ultrasonic probe configured to transmit/receive ultrasonic waves;
   a camera that captures a subject;
   an ultrasonic image generator configured to generate an ultrasonic image of the subject based on a reception signal acquired from the ultrasonic probe;
   a first hardware processor configured to generate a display image including both a camera image acquired from the camera and the ultrasonic image acquired from the ultrasonic image generator, and saves the display image in a storage; and
   a second hardware processor configured to decide a display style related to normal image display or mirror image display of the camera image to be arranged in the display image in accordance with an operation mode of the ultrasonic diagnostic apparatus, the operation mode including a live mode, a freeze mode, a moving image reproduction mode or a still image reproduction mode.

2. The ultrasonic diagnostic apparatus according to claim 1, wherein
in response to a command from a controller, the first hardware processor is further configured to change a display style related to normal image display or mirror image display of the camera image to be arranged in the display image.

3. The ultrasonic diagnostic apparatus according to claim 2, wherein
in a case where the ultrasonic image is stored as moving image data, the first hardware processor is further configured to store the display image so that the camera image is displayed as a mirror image when a moving image is reproduced.

4. The ultrasonic diagnostic apparatus according to claim 3, wherein
the first hardware processor is further configured to store the ultrasonic image as the moving image data in a case of receiving an operation for saving the display image from a user when the operation mode of the ultrasonic diagnostic apparatus is the live mode.

5. The ultrasonic diagnostic apparatus according to claim 2, wherein
in a case where the ultrasonic image is stored as still image data, the first hardware processor is further configured to store the display image so that the camera image is displayed as a normal image when a still image is reproduced.

6. The ultrasonic diagnostic apparatus according to claim 5, wherein
the first hardware processor is further configured to store the ultrasonic image as the still image data in a case of receiving an operation for saving the display image from a user when the operation mode of the ultrasonic diagnostic apparatus is the freeze mode.

7. The ultrasonic diagnostic apparatus according to claim 5, wherein
the first hardware processor is further configured to save the ultrasonic image as the still image data in a case where a user performs an input operation of annotation.

8. The ultrasonic diagnostic apparatus according to claim 5, wherein
the first hardware processor is further configured to save the ultrasonic image as the still image data in a case where a user performs an input operation for setting a body mark on the camera image.

9. The ultrasonic diagnostic apparatus according to claim 1, wherein
the display style of the camera image to be arranged in the display image is settable by a user in advance in association with an operation mode of the ultrasonic diagnostic apparatus.

10. The ultrasonic diagnostic apparatus according to claim 1, wherein
the first hardware processor is further configured to save the display image in the storage in a state where an explanatory display image indicating a mode of the display style of the camera image to be arranged in the display image is added within the display image, the mode of the display style including the normal image display or the mirror image display.

11. A control method of an ultrasonic diagnostic apparatus comprising:
generating an ultrasonic image of a subject based on a reception signal acquired from an ultrasonic probe;
generating a display image including a camera image acquired from a camera that captures the subject and the ultrasonic image, and saving the display image in a storage; and
deciding a display style related to normal image display or mirror image display of the camera image to be arranged in the display image in accordance with an operation mode of the ultrasonic diagnostic apparatus, the operation mode including a live mode, a freeze mode, a moving image reproduction mode or a still image reproduction mode.

12. A non-transitory recording medium storing a computer readable control program of an ultrasonic diagnostic apparatus causing a computer to execute processing of:
generating an ultrasonic image of a subject based on a reception signal acquired from an ultrasonic probe;
processing of generating a display image including a camera image acquired from a camera that captures the subject and the ultrasonic image, and reproducibly saving the display image in a storage; and
processing of deciding a display style related to normal image display or mirror image display of the camera image to be arranged in the display image in accordance with an operation mode of the ultrasonic diagnostic apparatus, the operation mode including a live mode, a freeze mode, a moving image reproduction mode or a still image reproduction mode.

13. The control method according to claim 11 further comprising:
adding an explanatory display image indicating a mode of the display style of the camera image to be arranged in the display image within the display image, the mode of the display style including the normal image display or the mirror image display.

14. The non-transitory recording medium according to claim 12 storing the computer readable control program of the ultrasonic diagnostic apparatus further causing the computer to execute processing of:
adding an explanatory display image indicating a mode of the display style of the camera image to be arranged in the display image within the display image, the mode of the display style including the normal image display or the mirror image display.

15. The ultrasonic diagnostic apparatus according to claim 1, wherein
the first hardware processor is further configured to add a probe mark in the camera image to identify a position of the ultrasonic probe in the camera image.

16. The ultrasonic diagnostic apparatus according to claim 1, wherein
the first hardware processor is further configured to add text annotation in the display image.

* * * * *